United States Patent
Komura et al.

(10) Patent No.: US 10,723,306 B2
(45) Date of Patent: Jul. 28, 2020

(54) CURTAIN AIRBAG DEVICE MOUNTING STRUCTURE AND CURTAIN AIRBAG DEPLOYMENT METHOD

(71) Applicant: TOYOTA JIDOSHA KABUSHIKI KAISHA, Toyota-shi, Aichi-ken (JP)

(72) Inventors: Takamichi Komura, Okazaki (JP); Osamu Fukawatase, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 132 days.

(21) Appl. No.: 16/014,424

(22) Filed: Jun. 21, 2018

(65) Prior Publication Data

US 2019/0039553 A1 Feb. 7, 2019

(30) Foreign Application Priority Data

Aug. 7, 2017 (JP) .................... 2017-152636

(51) Int. Cl.
*B60R 21/232* (2011.01)
*B60R 21/213* (2011.01)
(Continued)

(52) U.S. Cl.
CPC ........ *B60R 21/232* (2013.01); *A46B 11/0082* (2013.01); *A47F 5/04* (2013.01); *A47F 5/05* (2013.01); *A47F 5/106* (2013.01); *A47F 11/02* (2013.01); *A61B 5/02021* (2013.01); *A61B 5/151* (2013.01); *A61B 5/150022* (2013.01);
(Continued)

(58) Field of Classification Search
CPC .......................... B60R 21/232; B60R 21/213
See application file for complete search history.

(56) References Cited

U.S. PATENT DOCUMENTS 6,152,485 A    11/2000 Kato
7,766,370 B2 *  8/2010 Putcha .............. B60R 21/215
                                              280/728.3

(Continued)

FOREIGN PATENT DOCUMENTS

DE  10 2006 053 990 A1   5/2007
EP      2 151 360 A1     2/2010
(Continued)

OTHER PUBLICATIONS

U.S. Appl. No. 15/884,916, filed Jan. 31, 2018.
(Continued)

*Primary Examiner* — Faye M Fleming
(74) *Attorney, Agent, or Firm* — Oliff PLC

(57) ABSTRACT

A curtain airbag device mounting structure includes: a first pillar forming a part of a front pillar and extends substantially along a vehicle height direction; a second pillar forming another part of the front pillar, the second pillar being disposed on a rear side of a vehicle relative to the first pillar at a predetermined distance from the first pillar and extending substantially along the vehicle height direction; a transparent member bridged between the first pillar and the second pillar; and a curtain airbag device including a curtain airbag stored along a roof side rail and the second pillar, the curtain airbag being configured to inflate and deploy in a curtain-like fashion over a side portion of a cabin of the vehicle in case of a collision of the vehicle.

8 Claims, 7 Drawing Sheets

(51) Int. Cl.

| | |
|---|---|
| B60R 21/2338 | (2011.01) |
| B23K 20/00 | (2006.01) |
| B22D 11/06 | (2006.01) |
| E04G 13/02 | (2006.01) |
| B01J 19/00 | (2006.01) |
| E05B 83/38 | (2014.01) |
| A47F 5/04 | (2006.01) |
| B62D 25/04 | (2006.01) |
| B60J 5/04 | (2006.01) |
| B65D 51/16 | (2006.01) |
| D06F 57/02 | (2006.01) |
| E02F 9/08 | (2006.01) |
| B25D 17/30 | (2006.01) |
| E04B 2/52 | (2006.01) |
| F16M 11/28 | (2006.01) |
| G02B 6/44 | (2006.01) |
| B60R 21/21 | (2011.01) |
| H01L 21/768 | (2006.01) |
| H01L 29/739 | (2006.01) |
| B63B 3/52 | (2006.01) |
| H01L 21/762 | (2006.01) |
| A47F 11/02 | (2006.01) |
| B21D 47/01 | (2006.01) |
| E04B 2/38 | (2006.01) |
| A61B 5/151 | (2006.01) |
| H01H 35/30 | (2006.01) |
| B60R 13/02 | (2006.01) |
| H05K 7/20 | (2006.01) |
| B62J 1/08 | (2006.01) |
| E05C 7/04 | (2006.01) |
| G02B 23/18 | (2006.01) |
| G05D 23/12 | (2006.01) |
| A46B 11/00 | (2006.01) |
| B01J 29/04 | (2006.01) |
| F16K 99/00 | (2006.01) |
| G09F 15/00 | (2006.01) |
| B62K 19/36 | (2006.01) |
| B62D 25/20 | (2006.01) |
| B29C 65/54 | (2006.01) |
| A61B 5/15 | (2006.01) |
| B60H 1/24 | (2006.01) |
| A61M 5/14 | (2006.01) |
| A47F 5/05 | (2006.01) |
| B66F 7/02 | (2006.01) |
| G02F 1/1339 | (2006.01) |
| B60J 10/777 | (2016.01) |
| B62D 27/06 | (2006.01) |
| G02B 7/12 | (2006.01) |
| B60H 1/26 | (2006.01) |
| B60J 7/00 | (2006.01) |
| E04B 2/24 | (2006.01) |
| H01L 45/00 | (2006.01) |
| A47F 5/10 | (2006.01) |
| E04C 3/30 | (2006.01) |
| F16C 33/74 | (2006.01) |
| B23D 7/04 | (2006.01) |
| B62D 25/14 | (2006.01) |
| E04B 2/56 | (2006.01) |
| A61B 5/02 | (2006.01) |
| B65G 41/00 | (2006.01) |
| E04B 2/72 | (2006.01) |
| B21D 37/10 | (2006.01) |
| E04C 1/00 | (2006.01) |
| B60R 11/00 | (2006.01) |
| B60R 21/04 | (2006.01) |

(52) U.S. Cl.
CPC ...... *A61B 5/15045* (2013.01); *A61B 5/15134* (2013.01); *A61B 5/150419* (2013.01); *A61M 5/141* (2013.01); *B01J 19/0093* (2013.01); *B01J 29/049* (2013.01); *B21D 37/10* (2013.01); *B21D 47/01* (2013.01); *B22D 11/06* (2013.01); *B22D 11/0608* (2013.01); *B22D 11/0657* (2013.01); *B22D 11/0688* (2013.01); *B23D 7/04* (2013.01); *B23K 20/005* (2013.01); *B25D 17/30* (2013.01); *B29C 65/548* (2013.01); *B60H 1/243* (2013.01); *B60H 1/265* (2013.01); *B60J 5/0479* (2013.01); *B60J 7/0076* (2013.01); *B60J 10/7775* (2016.02); *B60R 13/025* (2013.01); *B60R 21/21* (2013.01); *B60R 21/213* (2013.01); *B60R 21/2338* (2013.01); *B62D 25/04* (2013.01); *B62D 25/147* (2013.01); *B62D 25/2036* (2013.01); *B62D 27/065* (2013.01); *B62J 1/08* (2013.01); *B62K 19/36* (2013.01); *B63B 3/52* (2013.01); *B65D 51/1611* (2013.01); *B65G 41/008* (2013.01); *B66F 7/02* (2013.01); *D06F 57/02* (2013.01); *E02F 9/08* (2013.01); *E04B 2/24* (2013.01); *E04B 2/38* (2013.01); *E04B 2/52* (2013.01); *E04B 2/56* (2013.01); *E04B 2/72* (2013.01); *E04C 1/00* (2013.01); *E04C 3/30* (2013.01); *E04G 13/02* (2013.01); *E05B 83/38* (2013.01); *E05C 7/04* (2013.01); *F16C 33/745* (2013.01); *F16K 99/0017* (2013.01); *F16M 11/28* (2013.01); *G02B 6/4438* (2013.01); *G02B 7/12* (2013.01); *G02B 23/18* (2013.01); *G02F 1/13394* (2013.01); *G05D 23/126* (2013.01); *G09F 15/00* (2013.01); *G09F 15/0075* (2013.01); *G09F 15/0081* (2013.01); *H01H 35/30* (2013.01); *H01L 21/76208* (2013.01); *H01L 21/76885* (2013.01); *H01L 29/7396* (2013.01); *H01L 45/1233* (2013.01); *H05K 7/20336* (2013.01); *B01J 2219/00367* (2013.01); *B01J 2220/84* (2013.01); *B01J 2220/86* (2013.01); *B60J 2005/0475* (2013.01); *B60R 2011/0022* (2013.01); *B60R 2021/0435* (2013.01); *B60R 2021/23382* (2013.01); *B62J 2001/085* (2013.01); *B63B 2701/12* (2013.01); *B65D 2501/24235* (2013.01); *E04B 2002/567* (2013.01); *H01L 2221/1026* (2013.01); *H01L 2224/40477* (2013.01); *H01L 2224/48477* (2013.01); *H01L 2224/77153* (2013.01); *H01L 2224/77318* (2013.01); *H01L 2224/77319* (2013.01); *H01L 2224/77821* (2013.01); *H01L 2224/78252* (2013.01); *H01L 2224/78263* (2013.01); *H01L 2224/78266* (2013.01); *H01L 2224/78282* (2013.01); *H01L 2224/78301* (2013.01); *H01L 2224/78306* (2013.01); *H01L 2224/78307* (2013.01); *H01L 2224/78349* (2013.01); *H01L 2224/78352* (2013.01); *H01L 2224/78502* (2013.01); *H01L 2224/78702* (2013.01); *H01L 2224/78705* (2013.01); *H01L 2224/78725* (2013.01); *H01L 2224/78735* (2013.01); *H01L 2224/78745* (2013.01); *H01L 2224/78756* (2013.01); *H01L 2224/78821* (2013.01); *H01L 2224/83102* (2013.01); *H01L 2224/85169* (2013.01); *H01L 2225/1058* (2013.01); *H05K 2203/0415* (2013.01)

(56) References Cited

U.S. PATENT DOCUMENTS

| | | | | |
|---|---|---|---|---|
| 7,934,746 | B2 * | 5/2011 | Glaser | B60R 13/025 |
| | | | | 280/728.3 |
| 9,387,821 | B1 * | 7/2016 | Saunders | B60R 21/215 |
| 2007/0108742 | A1 | 5/2007 | Itakura | |
| 2008/0238053 | A1 * | 10/2008 | Downey | B60R 21/232 |
| | | | | 280/730.2 |
| 2019/0233018 | A1 * | 8/2019 | Tanaka | B62D 25/04 |

FOREIGN PATENT DOCUMENTS

| | | |
|---|---|---|
| JP | H11-263184 A | 9/1999 |
| JP | 2006-273057 A | 10/2006 |
| JP | 2007-131262 A | 5/2007 |
| JP | 2007-196729 A | 8/2007 |
| JP | 2012-040963 A | 3/2012 |
| JP | 2014-037216 A | 2/2014 |
| JP | 2015-202783 A | 11/2015 |

OTHER PUBLICATIONS

U.S. Appl. No. 15/883,404, filed Jan. 30, 2018.
U.S. Appl. No. 15/883,679, filed Jan. 30, 2018.
U.S. Appl. No. 15/933,761, filed Mar. 23, 2018.

* cited by examiner

CURTAIN AIRBAG DEVICE MOUNTING STRUCTURE AND CURTAIN AIRBAG DEPLOYMENT METHOD

INCORPORATION BY REFERENCE

The disclosure of Japanese Patent Application No. 2017-152636 filed on Aug. 7, 2017 including the specification, drawings and abstract is incorporated herein by reference in its entirety.

BACKGROUND

1. Technical Field

The present disclosure relates to a curtain airbag device mounting structure and a curtain airbag deployment method.

2. Description of Related Art

Japanese Patent Application Publication No. 2006-273057 discloses a vehicle pillar structure. The vehicle pillar structure includes a front pillar (hereinafter referred to as "A-pillar") inner panel, an A-pillar frame provided so as to face the front pillar inner panel, and an A-pillar garnish provided on the vehicle cabin side (vehicle interior side) of the A-pillar inner panel, and a transparent member is held by the A-pillar inner panel and the A-pillar frame. An opening is formed so as to extend through the A-pillar inner panel, the A-pillar frame and the A-pillar garnish in a thickness direction, and a driver can view an object on the other side of the A-pillar from the opening through the transparent member.

SUMMARY

In general, a curtain airbag that in case of a collision of the relevant vehicle, inflates and deploys in a curtain-like fashion over a side portion of the vehicle cabin is partly stored in a space formed by an A-pillar inner panel and an A-pillar garnish, in a state before inflation and deployment. However, the vehicle pillar structure disclosed in JP2006-273057 A includes the opening in the A-pillar that is divided in a first pillar disposed on the vehicle front side in a front-rear direction of the vehicle and a second pillar disposed on the vehicle rear side in the front-rear direction of the vehicle with the opening therebetween. Therefore, a position at which a curtain airbag is stored is limited and may possibly affect inflation and deployment of the curtain airbag. Therefore, the aforementioned conventional technique has room for improvement in this point.

The present disclosure provides a curtain airbag device mounting structure and a curtain airbag deployment method that can ensure both wide view during driving of a vehicle and curtain airbag deployment capability.

A first aspect of the disclosure provides a curtain airbag device mounting structure including: a first pillar that forms a part of a front pillar and extends substantially along a vehicle height direction; a second pillar that forms another part of the front pillar, the second pillar being disposed on a rear side of a vehicle relative to the first pillar at a predetermined distance from the first pillar and extending substantially along the vehicle height direction; a transparent member that is bridged between the first pillar and the second pillar and enables an outside of the vehicle to be viewed from a driver seat; and a curtain airbag device including a curtain airbag stored along a roof side rail and the second pillar, the curtain airbag being configured to be supplied with gas to inflate and deploy in a curtain-like fashion over a side portion of a cabin of the vehicle in case of a collision of the vehicle.

According to the above aspect, the first pillar that forms a part of the A-pillar and is provided so as to extend substantially along the vehicle height direction, and a second pillar that forms another part of the A-pillar is disposed on the rear side of the vehicle relative to the first pillar at a predetermined distance from the first pillar and is provided so as to extend substantially along the vehicle height direction are provided. Therefore, a driver can view an object on the other side of the A-pillar from the transparent member bridged between the first pillar and the second pillar.

Also, the curtain airbag configured such that in case of a collision of the vehicle, the curtain airbag can be supplied with a gas to inflate and deploy in a curtain-like fashion over a side portion of the vehicle cabin is stored along the roof side rail and the second pillar. In other words, the curtain airbag is stored in a part of the A-pillar, the part being in the vicinity of a door opening, and in case of a collision of the vehicle, the curtain airbag can quickly be inflated and deployed over a side of an occupant and thereby hold the occupant.

Furthermore, as an example, if the curtain airbag is stored along the first pillar, when the curtain airbag inflates and deploys, the second pillar located on the vehicle rear side of the first pillar may hinder the inflation and deployment of the curtain airbag because the curtain airbag inflates and deploys in a curtain-like fashion over a side portion of the vehicle cabin. However, in the configuration according to the present disclosure, the curtain airbag is stored along the second pillar, and thus, the curtain airbag can smoothly inflate and deploy without being hindered by the second pillar.

In other words, according to the above aspect, an excellent effect of enabling ensuring both wide view during driving of the vehicle and capability of deployment of the curtain airbag is provided.

In the first aspect, the curtain airbag device may include a front pillar garnish attached to a vehicle interior side of the front pillar. The front pillar garnish may include a front-side garnish attached to the first pillar and a rear-side garnish formed separately from the front-side garnish and attached to the second pillar, the rear-side garnish being configured to cover the curtain airbag from a vehicle interior side of the curtain airbag and to hold the curtain airbag in a state in which the curtain airbag is apart from the second pillar.

According to the above configuration, the A-pillar garnish is attached to the vehicle interior side of the A-pillar. The A-pillar garnish includes the front-side garnish attached to the first pillar, and the rear-side garnish formed separately from the front-side garnish and attached to the second pillar. Also, the rear-side garnish is configured so as to cover the curtain airbag from the vehicle interior side and hold the curtain airbag in a state in which the curtain airbag is apart from the second pillar. Therefore, when the curtain airbag inflates and deploys, a deployment load of the curtain airbag is transferred only to the rear-side garnish and the deployment load causes the rear-side garnish to move apart from the second pillar and be held. Thus, the curtain airbag can smoothly be inflated and deployed in the vehicle cabin from between the second pillar and the rear-side garnish while breakage caused as a result of applying the deployment load locally to the A-pillar garnish and flying of the A-pillar garnish in the vehicle cabin are prevented.

In other words, the above configuration has an effect of enabling enhancement of the capability of deployment of the curtain airbag.

In the first aspect, the rear-side garnish may be attached to the second pillar via a tether clip.

According to the above configuration, the rear-side garnish is attached to the second pillar via a tether clip, and thus, flying of the rear-side garnish when the rear-side garnish moves apart from the second pillar as a result of inflation and deployment of the curtain airbag can be suppressed by the tether clip.

In other words, the above configuration has an excellent effect of enabling suppression of flying of the rear-side garnish, and thus, the A-pillar garnish during deployment of the curtain airbag.

In the first aspect, the front-side garnish may include an extension portion at an upper end portion of the front-side garnish in the vehicle height direction, the extension portion extending toward the rear side of the vehicle, and including a rear end portion covered by an upper end portion of the rear-side garnish in the vehicle height direction; and the tether clip may be attached to the extension portion at a position corresponding to the extension portion in the rear-side garnish.

According to the above configuration, the extension portion is provided at the upper end portion of the front-side garnish, the extension portion is provided so as to extend toward the rear side of the vehicle and the rear end portion is covered by the upper end portion of the rear-side garnish. In other words, the vehicle upper side of the space between the front-side garnish and the rear-side garnish has an outer appearance that is continuous with the front-side garnish and the rear end portion of the extension portion is covered by the rear-side garnish, enabling a terminal end to be unnoticeable to occupants and provision of a neat appearance.

Also, as the tether clip is provided at a position in the rear-side garnish, the position corresponding to the extension portion of the front-side garnish, floating-up of the rear-side garnish at the part in which the extension portion of the front-side garnish and the rear-side garnish are laid on each other can be suppressed.

In the first aspect, each of the front-side garnish and the rear-side garnish may have a U-shape in a section orthogonal to a longitudinal direction of the front pillar and at least one of a wire harness and a hose may be held between the front-side garnish and the first pillar, and a part of the curtain airbag device may be stored between the rear-side garnish and the second pillar.

According to the above configuration, each of the front-side garnish and the rear-side garnish has a substantially U-shape in a section orthogonal to the longitudinal direction of the A-pillar. Then, at least either of a wire harness and a hose is held between the front-side garnish and the first pillar, and a part of the curtain airbag device is stored between the rear-side garnish and the second pillar. In other words, a wire harness and a hose can efficiently be stored in the limited space between the A-pillar and the A-pillar garnish without hindering inflation and deployment of the curtain airbag.

In other words, the above configuration has an excellent effect of enabling enhancement in storage space efficiency.

In the first aspect, the second pillar may include a reaction force surface at a part on a vehicle interior side of the second pillar, the part facing the curtain airbag, a thickness direction of the reaction force surface being substantially along a vehicle width direction.

According to the above configuration, the reaction force surface, the thickness direction of which is substantially the width direction of the vehicle, is provided at the part on the vehicle interior side of the second pillar, the part facing the curtain airbag. In other words, the reaction force surface is provided in the vicinity of the curtain airbag. Therefore, when the curtain airbag inflates and deploys, the curtain airbag can promptly receive a reaction force of the deployment from the reaction force surface, enabling the curtain airbag to be quickly deployed toward the inner side substantially in the width direction of the vehicle, that is, the inner side of the vehicle cabin.

In other words, the above configuration has an excellent effect of enabling further enhancement in capability of deployment of the curtain airbag.

In the first aspect, the second pillar may include: a pillar inner panel that forms a part of the second pillar and has a L-shape in a section orthogonal to a longitudinal direction, the L-shape being formed by the reaction force surface and a extending surface, the extending surface extending outward in the vehicle width direction from the reaction force surface; and a pillar outer panel that forms another part of the second pillar, an end surface of at least one of end portions of the pillar inner panel in a direction orthogonal to a longitudinal direction of the pillar inner panel being in contact with a surface of an end portion of the pillar outer panel in a direction orthogonal to a longitudinal direction of the pillar outer panel.

According to the above configuration, the pillar inner panel that forms a part of the second pillar and has a L-shape in a section orthogonal to the longitudinal direction, the L-shape being formed by the reaction force surface and the surface provided so as to extend from the reaction force surface toward the outer side in the width direction of the vehicle, and an end surface of at least one of end portions in the direction orthogonal to the longitudinal direction abuts on a surface of an end portion in the direction orthogonal to the longitudinal direction of the pillar outer panel that forms the other part of the second pillar. Therefore, the need for a flange for joining the pillar outer panel and the pillar inner panel, the flange projecting to the outside of the A-pillar, is eliminated at least for one of end portions in the direction orthogonal to the longitudinal direction of the second pillar of the A-pillar.

In other words, the above configuration has an excellent effect of enabling securing wider view during driving of the vehicle.

In the first aspect, a part of the second pillar, the part facing the curtain airbag, may include a substantially flat surface.

According to the above configuration, the part of the second pillar, the part facing the curtain airbag, includes a substantially flat surface, and thus, storage space efficiency of the accommodation space for the curtain airbag, the accommodation space being formed by the second pillar and the A-pillar garnish, can be enhanced.

In other words, the above configuration has an excellent effect of enabling enhancement in mountability of the curtain airbag.

A second aspect of the disclosure provides a curtain airbag deployment method. The curtain airbag deployment method according to the second aspect is performable by a structure mounting a curtain airbag device including a rear-side garnish that forms a part of a front pillar garnish and has a U-shape that opens to a front pillar side in a section orthogonal to a longitudinal direction, the U-shape being formed by a first side wall portion and a second side wall portion facing the first side wall portion, a curtain airbag stored in a folded state between the rear-side garnish and a pillar inner panel, and an inflator that activates to supply a gas to the curtain airbag upon detection or prediction of a collision of a relevant vehicle. The curtain airbag deployment method includes: holding the rear-side garnish in a state in which the rear-side garnish is apart from the front pillar via initial inflation of the curtain airbag caused by the activation of the inflator, after the initial inflation, causing the curtain airbag to inflate and deploy from a gap between the rear-side garnish and the front pillar while pressing the first side wall portion and the second side wall portion of the rear-side garnish apart from each other; and after causing the curtain airbag to inflate and deploy from a gap between the rear-side garnish and the front pillar, inflating and deploying the curtain airbag toward an inner side of an interior of the vehicle from between the first side wall portion and the second side wall portion pressed apart from each other to inflate and deploy the curtain airbag in a curtain-like fashion over a side portion of the interior of the vehicle while withdrawing the rear-side garnish.

According to the above configuration, upon activation of the inflator, the rear-side garnish is held in a state in which the rear-side garnish is apart way from the A-pillar via initial inflation of the curtain airbag. Then, the curtain airbag inflates and deploys from the gap between the rear-side garnish and the A-pillar while pressing the first side wall portion and the second side wall portion of the rear-side garnish apart from each other. Then, the curtain airbag is inflated and deployed toward the inner side of the vehicle cabin from between the first side wall portion and the second side wall portion pressed apart from each other to inflate and deploy in a curtain-like fashion over a side portion of the vehicle cabin while withdrawing the rear-side garnish. In other words, even where the rear-side garnish of the A-pillar garnish has a substantially U-shape in a section orthogonal to the longitudinal direction so as to cover the curtain airbag in a normal state, the curtain airbag can be inflated and deployed in a curtain-like fashion over a side portion of the cabin of the vehicle. In other words, the above configuration has an excellent effect of enabling ensuring both wide view during driving of the vehicle and capability of deployment of the curtain airbag.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

An embodiment of a curtain airbag device mounting structure according to the present disclosure will be described below with reference to FIGS. 1 to 7. Arrow FR indicated in each drawing denotes the front side in a front-rear direction of a vehicle, arrow OUT denotes the outer side in a width direction of the vehicle, and arrow UP denotes the upper side in a vehicle height direction.

Figure 1:
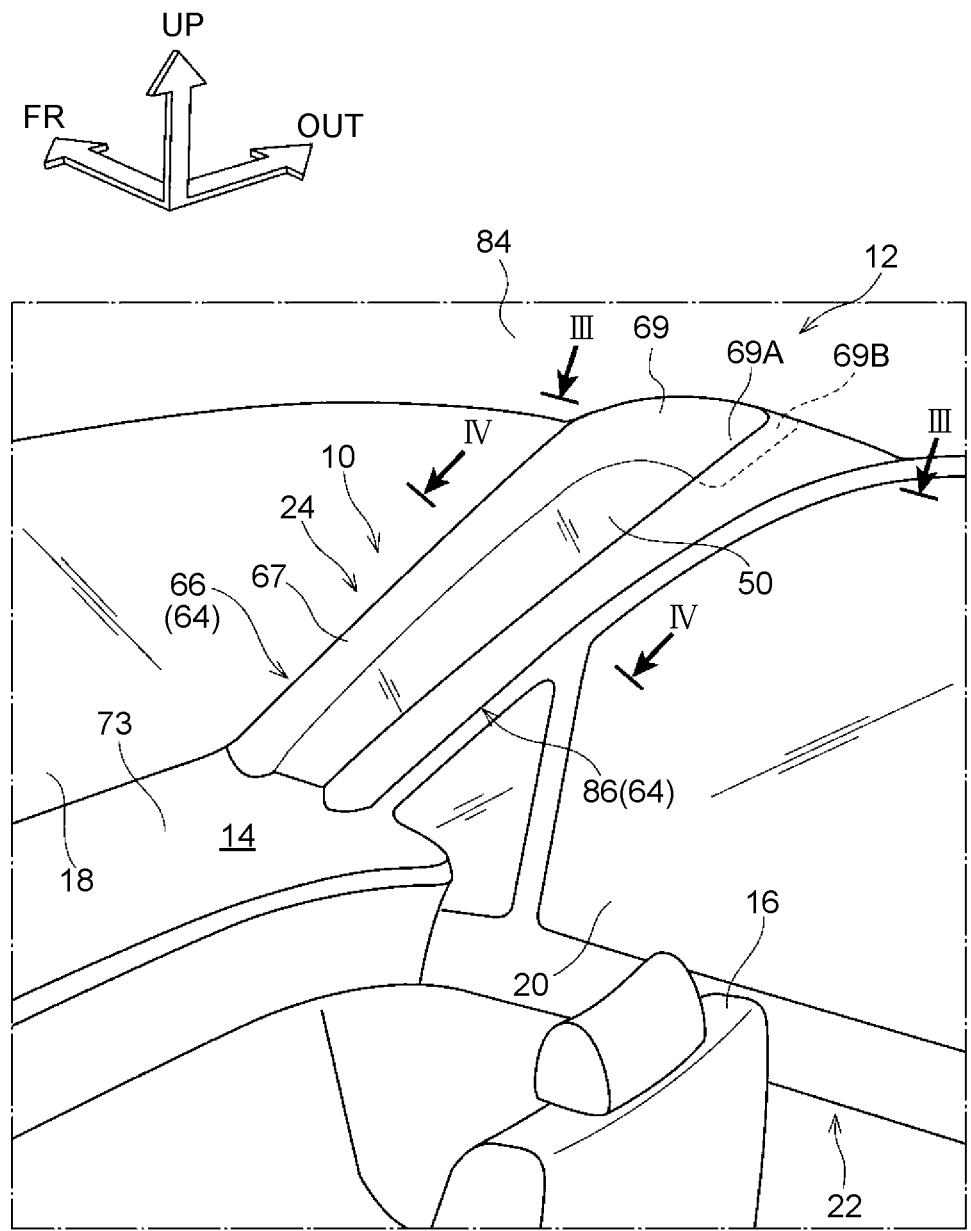
FIG. 1 is a schematic perspective diagram illustrating a cabin of a vehicle including a curtain airbag device mounting structure according to an embodiment.

As illustrated in FIG. 1, on the front side of a cabin 14 of a vehicle 12 to which a curtain airbag device mounting structure 10 according to the present embodiment is applied, a left-right pair of vehicle seats 16 are arranged, and a not-illustrated driver can sit on one of the vehicle seats 16. Here, as an example, the vehicle 12 in the present embodiment is a left-hand drive vehicle, and in the figure, illustration of the vehicle seat 16 on the driver's seat side is omitted.

On the vehicle front side relative to the vehicle seat 16, a front windshield (hereinafter simply referred to as "front windshield") 18 is provided. The front windshield 18 is a transparent window member that separates the inside of the cabin 14 and the outside of the cabin 14 from each other, and has a thickness substantially in the front-rear direction of the vehicle, and is further inclined toward the rear side of the vehicle further on the upper side of the vehicle in side view. An upper end portion of the front windshield 18 is connected to a front header (not illustrated) forming a front end portion of a roof including a roof panel 19 (see FIG. 3). Also, a lower end portion of the front windshield 18 is disposed so as to face, in the front-rear direction of the vehicle, a rear end portion of a hood that covers a power unit room provided on the front side of the vehicle from the upper side of the vehicle, and is connected to a cowl extending in the width direction of the vehicle (neither of both the hood and the cowl illustrated).

The front windshield 18 is formed so as to have a constant thickness, and has a gently curved shape such that an intermediate part, in the width direction of the vehicle, of the front windshield 18 projects toward the front side of the vehicle. Paired left and right A-pillars 24 are provided on respective outer sides, in the width direction of the vehicle, of the front windshield 18 and the front sides of respective front doors 22 each including a front side window 20.

The paired left and right A-pillars 24 each extend along a relevant end portion, in the width direction of the vehicle, of the front windshield 18, substantially with the vehicle height direction as a longitudinal direction thereof. In other words, the paired left and right A-pillars 24 are inclined toward the rear side of the vehicle further on the upper side of the vehicle. Hereinafter, description of the A-pillar 24 on the front passenger seat side will be provided; however, the A-pillar 24 on the opposite side of the front passenger seat (driver's seat) has a configuration that is similar to that of the A-pillar 24 on the front passenger seat side.

Figure 4:
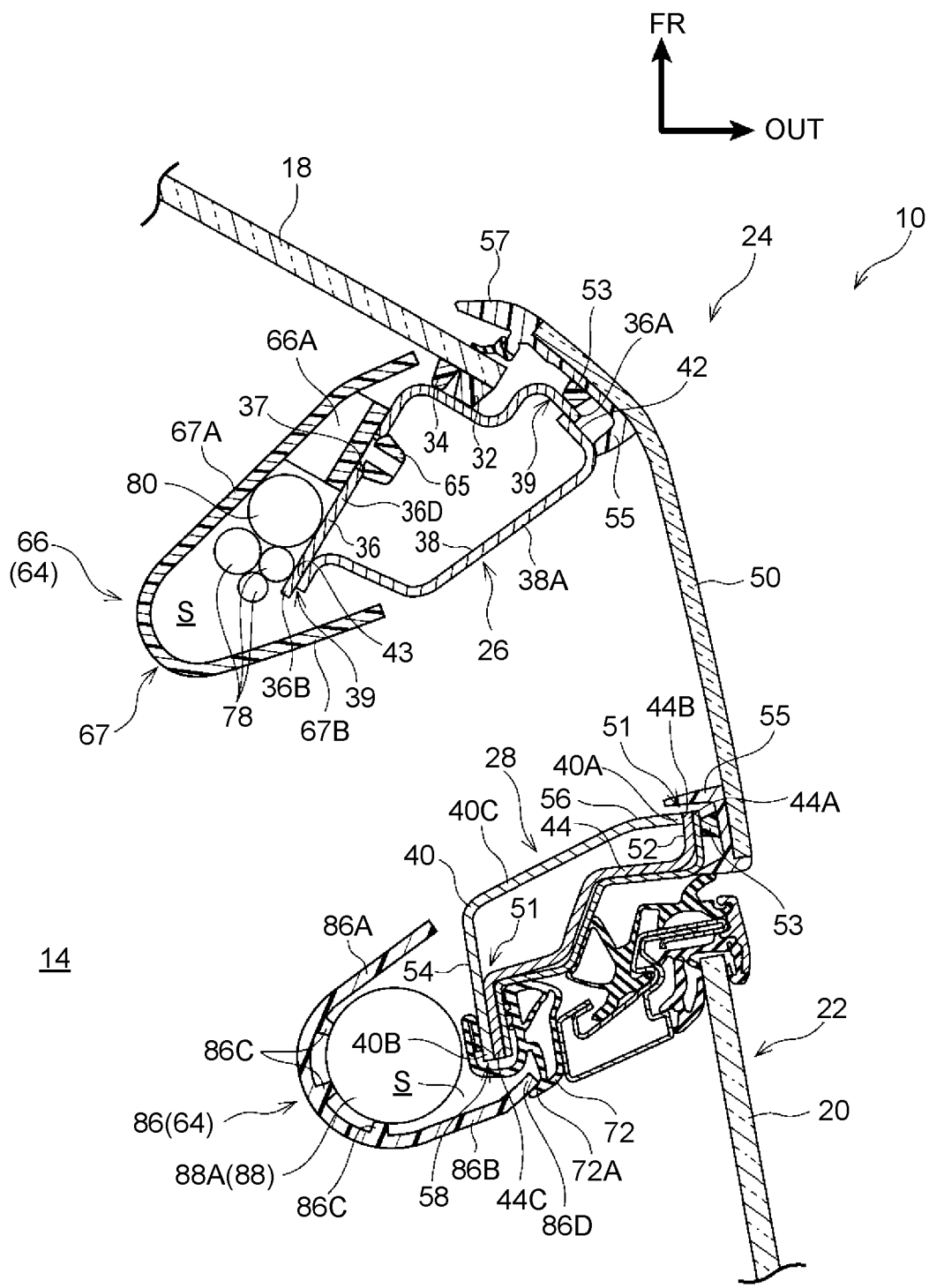
FIG. 4 is an enlarged sectional view along line IV-IV of FIG. 1.

As illustrated in FIG. 4, the A-pillar 24 includes a first pillar 26 and a second pillar 28. The first pillar 26 extends substantially along the vehicle height direction, and an end portion 30, in the width direction of the vehicle, of the front windshield 18 is joined to the first pillar 26 via a urethane adhesive 32 and a cushion rubber 34. The first pillar 26 includes a first pillar inner panel 36 made of a steel plate, which serves as a pillar inner panel, and a first pillar outer panel 38 made of a steel plate, which serves as a pillar outer panel. The first pillar inner panel 36 has a substantially crank-like shape in a section orthogonal to a longitudinal direction (direction substantially along the vehicle height direction). The first pillar outer panel 38 has a substantially U-shape that opens toward the inner side substantially in the width direction of the vehicle in a section orthogonal to a longitudinal direction (direction substantially along the vehicle height direction). The first pillar outer panel 38 forms a closed section jointly with the first pillar inner panel 36. In other words, the first pillar inner panel 36 is provided on the front side, substantially in the front-rear direction of the vehicle, of the first pillar outer panel 38 so as to face the first pillar outer panel 38, and the first pillar outer panel 38 and the first pillar inner panel 36 are joined to each other via weld portions 39.

At the weld portions 39, respective end portions 36A, 36B in a lateral direction of the first pillar inner panel 36 is laid on and welded to respective flat surfaces 42, 43, which are flat surfaces in an in-plane direction of the first pillar outer panel 38.

The second pillar 28 is disposed substantially on the rear side of the vehicle relative to the first pillar 26. More specifically, the second pillar 28 is disposed at a predetermined distance from the first pillar 26 substantially in the front-rear direction of the vehicle. The predetermined distance is set to be equal to or longer than the distance between the centers of the pupils of a driver sat on the vehicle seat 16. Here, the "distance between the centers of the pupils" refers to the distance between the center of the pupil of the right eye (not illustrated) and the center of the pupil of the left eye (not illustrated) of a driver, and for example, approximately 60 to 65 mm in Japanese adults. In the present embodiment, as an example, the predetermined distance is set as 65 mm.

Also, the second pillar 28 extends substantially in parallel to the first pillar 26 (substantially along the vehicle height direction), and includes a second pillar inner panel 40 made of a steel plate, which serves as a pillar inner panel, and a second pillar outer panel 44 made of a steel plate, which serves as a pillar outer panel. The second pillar inner panel 40 has a substantially L-shape in a section orthogonal to a longitudinal direction (substantially along the vehicle height direction). The second pillar outer panel 44 has a substantially crank-like shape in a section orthogonal to a longitudinal direction (substantially along the vehicle height direction). The second pillar outer panel 44 forms a closed section jointly with the second pillar inner panel 40. In other words, the second pillar inner panel 40 is provided substantially on the front side of the second pillar outer panel 44 so as to face the second pillar outer panel 44, and the second pillar outer panel 44 and the second pillar inner panel 40 are joined to each other via weld portions 51.

At a weld portion 51, an end portion 40A in a lateral direction (direction orthogonal to the longitudinal direction) of the second pillar inner panel 40 is abutted on and welded to a flat surface 52, which is a flat surface in an in-plane direction of an end portion 44A in a lateral direction (direction orthogonal to the longitudinal direction) of the second pillar outer panel 44. Consequently, an outer surface 56 of the end portion 40A of the second pillar inner panel 40 and an end surface 44B of the end portion 44A in the lateral direction of the second pillar outer panel 44 are disposed so as to be substantially flush with each other. Also, at a weld portion 51, an end portion 44C in a lateral direction of the second pillar outer panel 44 is laid on and welded to a flat wall 54, which is a flat surface of the second pillar inner panel 40 and serves as a reaction force surface. The flat wall 54 is provided so as to extend substantially with the width direction of the vehicle as a thickness direction thereof.

An opening trim 72 is attached to a part in which the end portion 40B in the lateral direction of the second pillar inner panel 40 and the end portion 44C in the lateral direction of the second pillar outer panel 44 are in abutment with each other, that is, a flange 58. The opening trim 72 is positioned at a position at which the opening trim 72 is in abutment with the second pillar outer panel 44. Also, a seal member of the front door 22 can be brought into abutment with the second pillar outer panel 44. Also, a width dimension of each of the first pillar 26 and the second pillar 28 substantially in a horizontal direction as viewed from an eye point (not illustrated) of a driver is set to be equal to or smaller than the distance between the centers of the pupils of the driver.

An A-pillar outer glass member 50 is bridged between the first pillar 26 and the second pillar 28 from the outer side substantially in the width direction of the vehicle via urethane adhesives 53 and cushion rubbers 55. The A-pillar outer glass member 50 is a transparent window member substantially with the width direction of the vehicle as a thickness direction thereof, and is inclined toward the rear side of the vehicle further on the upper side of the vehicle in side view (see FIG. 1). A seal member 57 is provided between the A-pillar outer glass member 50 and the front windshield 18, and the seal member 57 suppresses entry of, e.g., rain water into between the A-pillar outer glass member 50 and the front windshield 18. Also, the A-pillar outer glass member 50 is not limited to one made of glass and may be formed of, e.g., a transparent fiber-reinforced resin.

An A-pillar garnish 64 is provided on the inner sides, in the width direction of the vehicle, of the first pillar 26 and the second pillar 28. The A-pillar garnish 64, which is made of a resin, and includes a front-side garnish 66 provided on the vehicle cabin side of the first pillar 26, and a rear-side garnish 86 provided on the vehicle cabin side of the second pillar 28.

As illustrated in FIG. 1, the front-side garnish 66 includes a body portion 67 provided so as to extend substantially in the vehicle height direction along the first pillar 26 illustrated in FIG. 4, and an extension portion 69 provided at an upper end portion of the body portion 67 so as to extend substantially toward the rear side of the vehicle. As illustrated in FIG. 4, at an outer side (back side), in the width direction of the vehicle, of the body portion 67, a plurality of clip seats 66A and clips 65 attached to the clip seats 66A are provided along a longitudinal direction so as to be spaced from each other. The clip seats 66A are provided so as to face a wall portion 36D on the inner side, substantially in the width direction of the vehicle, of the first pillar inner panel 36. Then, as a result of the clips 65 attached to the respective clip seats 66A being inserted into through-holes 37 formed so as to extend through the wall portion 36D on the inner side substantially in the width direction of the vehicle, in a thickness direction, the front-side garnishes 66 are attached to the first pillar 26. Here, an end portion, on the lower side of the vehicle, of the body portion 67 is inserted in a not-illustrated slot formed in an instrumental panel 73, which is illustrated in FIG. 1 (see FIG. 1).

The body portion 67 of the front-side garnish 66 has a substantially U-shape that opens toward the outer side substantially in the width direction of the vehicle, in a section orthogonal to the longitudinal direction of the body portion 67, the substantially U-shape being formed by a first side wall portion 67A covering the first pillar inner panel 36 from the front side of the vehicle and a second side wall portion 67B facing the first side wall portion 67A. An accommodation space S is formed between the first side wall portion 67A and the first pillar inner panel 36, and wire harnesses 78 and a hose 80 are held in the accommodation space S. Also, the second side wall portion 67I is spaced from a surface 38A, on the rear side of the vehicle, of the first pillar outer panel 38 and is provided so as to be substantially flush with the vehicle rear side surface 38A.

Figure 3:
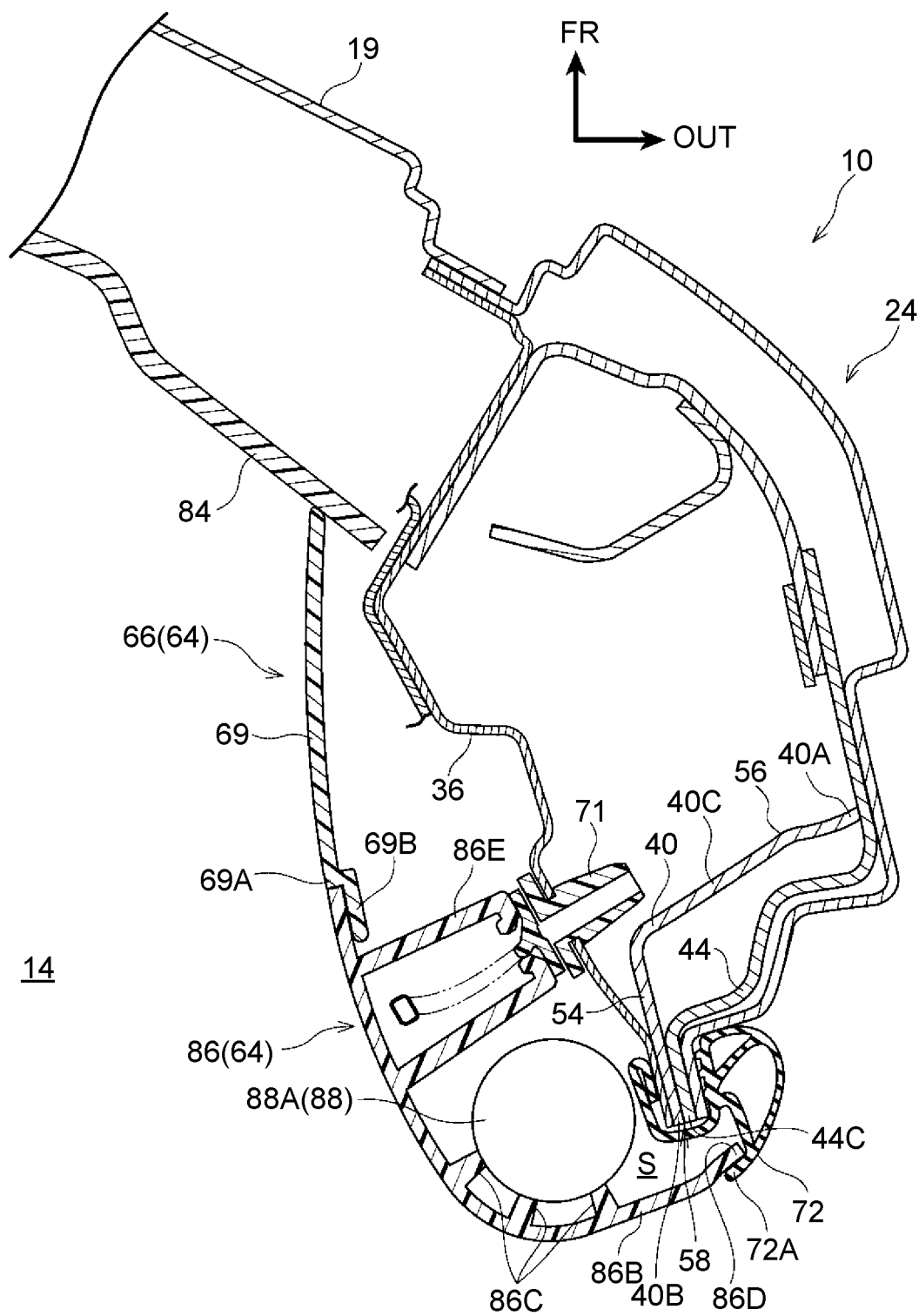
FIG. 3 is an enlarged sectional view along line III-II of FIG. 1.

As illustrated in FIG. 1, the extension portion 69 of the front-side garnish 66 is formed integrally with the body portion 67, and an end portion, on the upper side of the vehicle, of the extension portion 69 is in abutment with a roof head liner 84. As illustrated in FIG. 3, a step portion 69B provided so as to extend on the outer side substantially in the width direction of the vehicle relative to a general wall portion of the extension portion 69 is formed at the rear end portion 69A of the extension portion 69. An upper end portion of the rear-side garnish 86 is in abutment with the step portion 69B so as to be laid on the step portion 69B, whereby in a surface on the inner side, in the width direction of the vehicle, of the general wall portion of the extension portion 69 and a surface on the inner side, in the width direction of the vehicle, of the upper end portion of the rear-side garnish 86 are disposed so as to be substantially flush with each other.

The rear-side garnish 86 is provided so as to extend substantially in the vehicle height direction along the second pillar 28. As illustrated in FIG. 3, the rear-side garnish 86 has a substantially U-shape that opens toward the outer side substantially in the width direction of the vehicle in a section orthogonal to a longitudinal direction, the substantially U-shape being formed by a first side wall portion 86A provided so as to extend substantially in the width direction of the vehicle and a second side wall portion 86B facing the first side wall portion 86A. The first side wall portion 86A is spaced from a surface 40C, on the front side of the vehicle, of the second pillar inner panel 40 of the second pillar 28 and is provided so as to be substantially flush with the vehicle front side surface 40C. Also, the second side wall portion 86B is provided so as to be extend over the vehicle rear side of the flange 58 and the outer side, in the width direction of the vehicle, of the flange 58 and is arranged such that an end portion 86D in the width direction of the vehicle is laid on a lip portion 72A of the opening trim 72 in the front-rear direction of the vehicle. Furthermore, a plurality of ribs 86C projecting to the outer side substantially in the width direction of the vehicle along a thickness direction are formed at a part between the first side wall portion 86A and the second side wall portion 86B of the rear-side garnish 86.

As illustrated in FIG. 3, a clip seat 86E and a tether clip 71 attached to the clip seat 86E are provided at a surface on the outer side in the width direction of the vehicle (back surface) of the rear-side garnish 86. More specifically, the clip seat 86E and the tether clip 71 are provided at a part of the rear-side garnish 86, the part corresponding to the extension portion 69 of the front-side garnish 66. A basic configuration of the tether clip 71 is substantially similar to configurations known through, for example, Japanese Patent Application Publication No. 2015-202783, etc., and thus, detailed description thereof will be omitted.

Also, a clip seat 66A and a clip 65 attached to the clip seat 66A (see FIG. 4) each having a configuration that is similar to that of the front-side garnish 66 is provided at a substantially intermediate portion in a longitudinal direction of the rear-side garnish 86 (not illustrated).

The tether clip 71 attached to the clip seat 86E provided in the rear-side garnish 86 is inserted in a through-hole formed so as to extend through the first pillar inner panel 36 in a thickness direction, the first pillar inner panel 36 being joined to the flat wall 54 of the second pillar inner panel 40 from the inner side in the width direction of the vehicle. Also, although not illustrated, other than the tether clip 71 attached to the clip seat 86E in the rear-side garnish 86, the clip 65 attached to the clip seat 66A is inserted in a through-hole formed so as to extend through the flat wall 54 of the second pillar inner panel 40 in a thickness direction. With the above configuration, the rear-side garnish 86 is attached to the second pillar 28. Here, as with the front-side garnish 66, an end portion, on the lower side of the vehicle, of the rear-side garnish 86 is inserted in the not-illustrated slot formed in the instrumental panel 73 illustrated in FIG. 1 (see FIG. 1).

A curtain airbag device 88 includes a curtain airbag 88A, a tension strap 96 (see FIG. 2) and an inflator 88B. The curtain airbag 88A is formed so as to, upon supply of a gas from the inflator 88B, inflate and deploy along a side portion of the vehicle cabin and cover the front side window 20 (see FIG. 4) and a B-pillar (center pillar) 91 (see FIG. 2).

Figure 2:
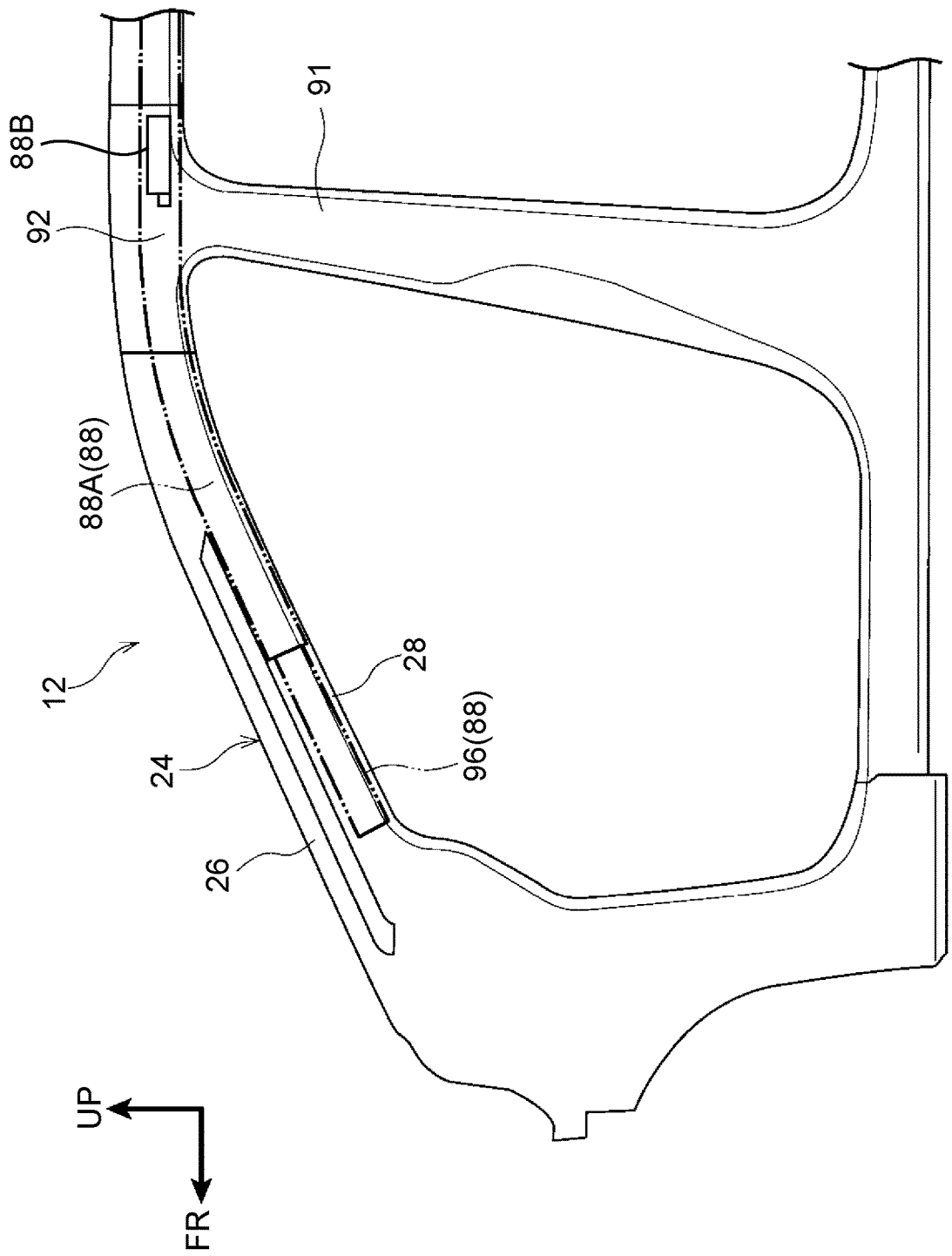
FIG. 2 is a side view illustrating a vehicle body frame of a vehicle including a curtain airbag device mounting structure according to an embodiment as viewed from the outer side in a width direction of the vehicle.

In normal times, as illustrated in FIG. 2, the curtain airbag 88A is folded in an elongated shape and stored together with the inflator 88B in a roof side rail 92 provided at an upper end portion of the side portion of the vehicle cabin. In the stored state, the curtain airbag 88A folded in the elongated shape extends from a substantially intermediate portion in a longitudinal direction of the second pillar 28 in the A-pillar 24 to the upper end side of a not-illustrated C-pillar (rear pillar) along the roof side rail 92. A basic configuration of the curtain airbag 88A is substantially similar to configurations known through, for example, Japanese Patent Application No. 2012-40963, etc., and detailed description thereof will be omitted.

As illustrated in FIGS. 3 and 4, the curtain airbag 88A arranged along the second pillar 28 is accommodated in an accommodation space S formed by the rear-side garnish 86 and the second pillar 28, in abutment with distal end portions of the ribs 86C of the rear-side garnish 86.

Also, on the vehicle front side of the curtain airbag 88A, the tension strap 96 is provided. The tension strap 96 is provided so as to extend along the second pillar 28, and an end portion, on the front side of the vehicle, of the tension strap 96 is attached to an end portion, on the front side of the vehicle, of the second pillar 28 (see FIG. 2).

Operation and Effects

Next, operation and effects of the present embodiment will be described.

Figure 5:
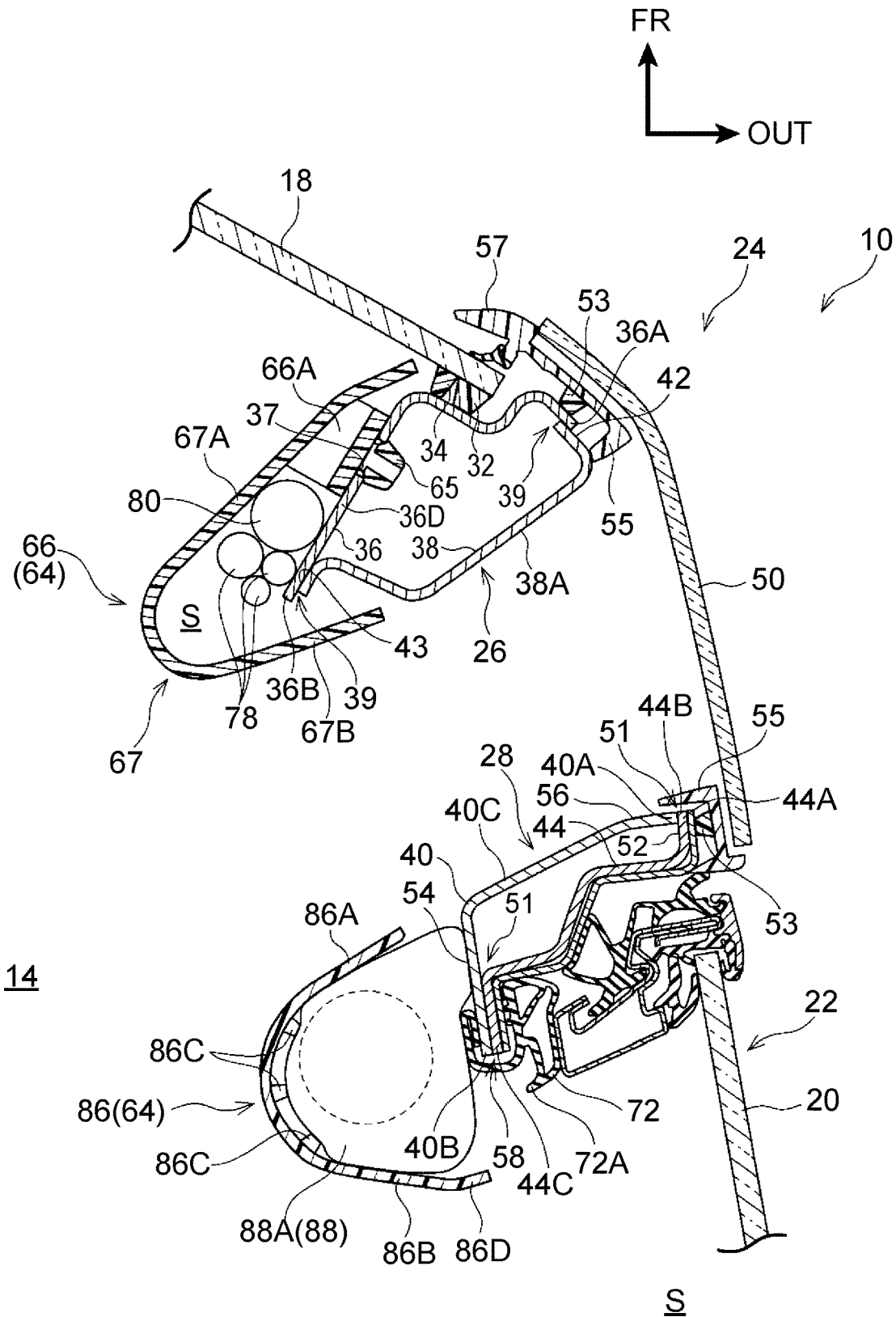
FIG. 5 is an enlarged sectional view corresponding to FIG. 4, the sectional view illustrating an initial state during inflation and deployment of a curtain airbag in a vehicle including a curtain airbag device mounting structure according to an embodiment.

Upon detection of a collision of the vehicle by a not-illustrated airbag sensor and output of a collision signal to a not-illustrated controller, the controller applies a predetermined current to the inflator 88B if the controller determines such current application as necessary based on the input collision signal. Consequently, as illustrated in FIG. 5, the inflator 88B activates and a gas thereby flows into the curtain airbag 88A in the folded state. As a result, initial inflation of the curtain airbag 88A causes the curtain airbag 88A to receive a reaction force from the flat wall 54 and transfers a deployment load to the rear-side garnish 86, and thus the rear-side garnish 86 is moved apart from the second pillar 28 and held within a range allowed by the tether clip 71. Concurrently, the inflating and deploying curtain airbag 88A causes the first side wall portion 86A and the second side wall portion 86B of the rear-side garnish 86 to be pressed apart in a direction in which the first side wall portion 86A and the second side wall portion 86B move apart from each other.

Figure 6:
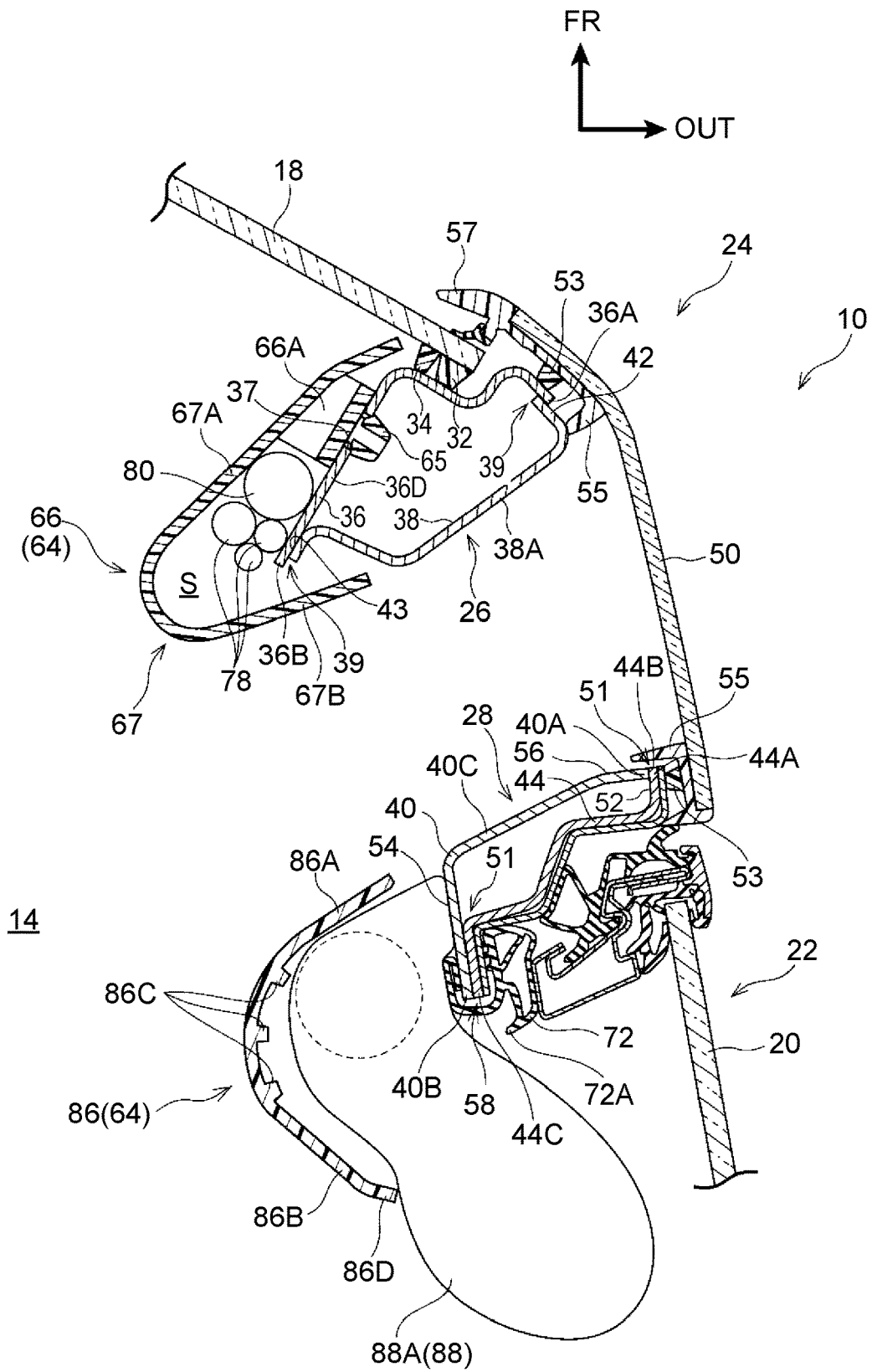
FIG. 6 is an enlarged sectional view corresponding to FIG. 4, the sectional view illustrating an intermediate state during inflation and deployment of a curtain airbag in a vehicle including a curtain airbag device mounting structure according to an embodiment.
Figure 7:
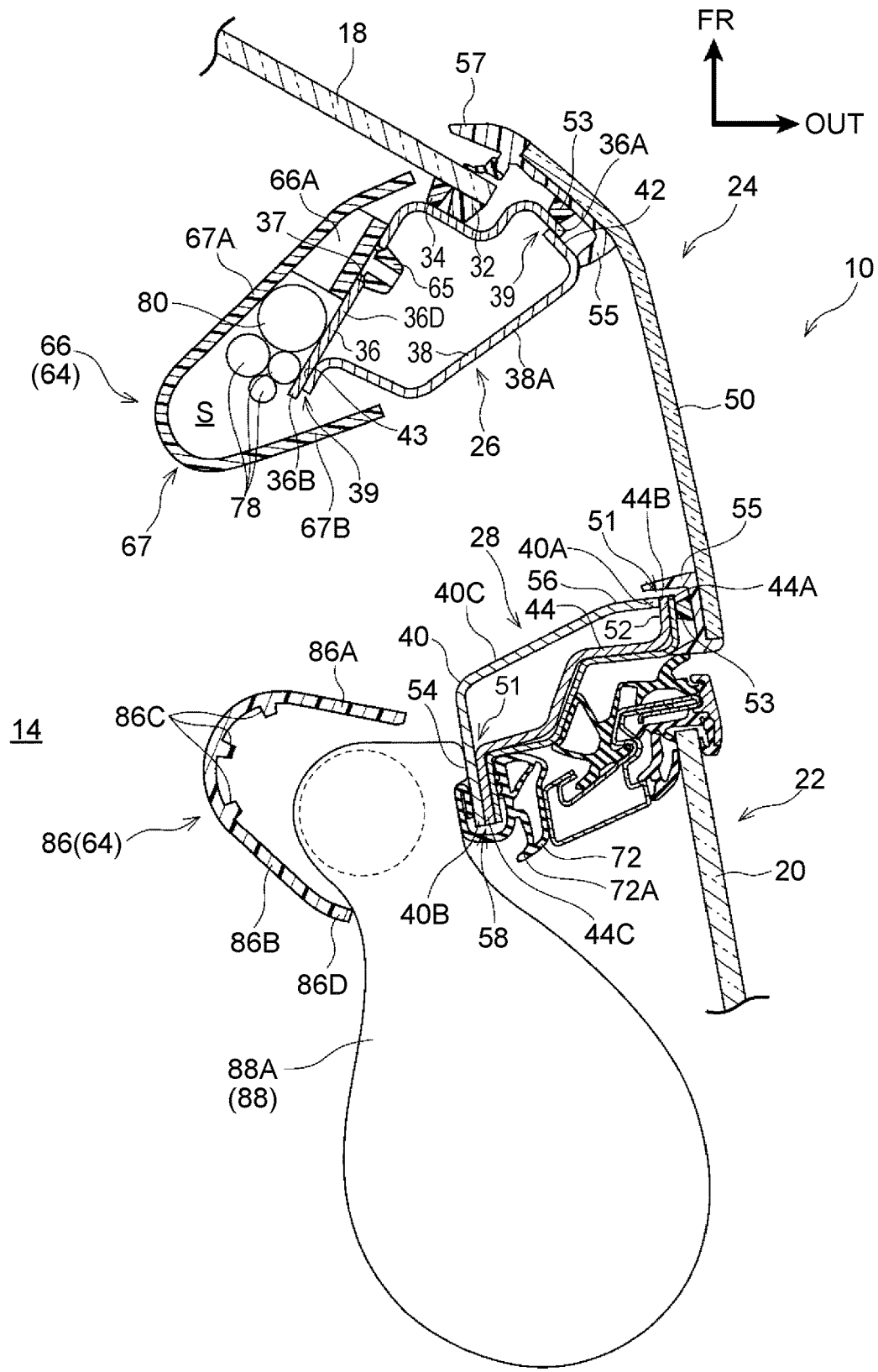
FIG. 7 is an enlarged sectional view corresponding to FIG. 4, the sectional view illustrating a late state during inflation and deployment of a curtain airbag of a vehicle including a curtain airbag device mounting structure according to an embodiment.

As illustrated in FIG. 6, upon the first side wall portion 86A and the second side wall portion 86B of the rear-side garnish 86 moving apart from each other, the curtain airbag 88A inflates and deploys toward the inner side of the vehicle cabin from the gap between the rear-side garnish 86 and the A-pillar 24. Then, as illustrated in FIG. 7, the curtain airbag 88A inflates and deploys in a curtain-like fashion over a side of the vehicle cabin while slightly turning and thereby withdrawing the rear-side garnish 86 substantially toward the front side of the vehicle. In other words, even where the rear-side garnish 86 of the A-pillar garnish 64 has a substantially U-shape in a section orthogonal to the longitudinal direction so as to cover the curtain airbag 88A in a normal state, the curtain airbag 88A can be inflated and deployed in a curtain-like fashion over a side portion of the vehicle cabin.

As described above, in the present embodiment, as illustrated in FIG. 1, the first pillar 26 that forms a part of the A-pillar 24 and is provided substantially along the vehicle height direction, and the second pillar 28 that forms the other part of the A-pillar 24, and is disposed on the rear side of the vehicle relative to the first pillar 26 at a predetermined distance from the first pillar 26 and is provided so as to extend substantially along the vehicle height direction. Therefore, a driver can view an object on the other side of the A-pillar 24, from between the first pillar 26 and the second pillar 28 via the A-pillar outer glass member 50.

Also, as illustrated in FIG. 2, the curtain airbag 88A configured so as to be able to inflate and deploy in a curtain-like fashion over a side portion of the vehicle cabin when the curtain airbag 88A is supplied with a gas in case of a collision of the vehicle is stored along the roof side rail 92 and the second pillar 28. In other words, the curtain airbag 88A is stored in a part of the A-pillar 24, the part being in the vicinity of a door opening, and thus, in case of a collision of the vehicle, the curtain airbag 88A can quickly be inflated and deployed over a side of an occupant and thereby hold the occupant.

Furthermore, as an example, if the curtain airbag 88A is stored along the first pillar 26, when the curtain airbag 88A inflates and deploys, the second pillar 28 located on the vehicle rear side of the first pillar 26 may hinder the inflation and deployment of the curtain airbag 88A because the curtain airbag 88A inflates and deploys in a curtain-like fashion over a side portion of the vehicle cabin. However, in the configuration of the present disclosure, the curtain airbag 88A is stored along the second pillar 28, and thus, the curtain airbag 88A can smoothly inflate and deploy without being hindered by the second pillar 28. Consequently, both wide view during driving of the vehicle and capability of deployment of the curtain airbag 88A can be ensured.

Still furthermore, the A-pillar garnish 64 is attached to the vehicle cabin side of the A-pillar 24. The A-pillar garnish 64 includes the front-side garnish 66 attached to the first pillar 26, and the rear-side garnish 86 formed separately from the front-side garnish 66 and attached to the second pillar 28. Also, the rear-side garnish 86 is configured so as to be able to cover the curtain airbag 88A from the vehicle cabin side and move apart from the second pillar 28. Therefore, when the curtain airbag 88A inflates and deploys, a deployment load of the curtain airbag 88A is transferred only to the rear-side garnish 86 and the deployment load causes the rear-side garnish 86 to move apart from the second pillar 28 (see FIG. 5). Thus, the curtain airbag 88A can be inflated and deployed in the vehicle cabin 14 from between the second pillar 28 and the rear-side garnish 86 while breakage caused as a result of applying the deployment load locally to the A-pillar garnish 64 is prevented (see FIGS. 6 and 7). Consequently, the capability of deployment of the curtain airbag 88A can be enhanced.

Also, as illustrated in FIG. 3, since the rear-side garnish 86 is attached to the second pillar 28 via the tether clip 71, when the rear-side garnish 86 moves apart from the second pillar 28 as a result of inflation and deployment of the curtain airbag 88A, the state in which the rear-side garnish 86 is apart from the second pillar 28 is held by the tether clip 71. Therefore, in case of deployment of the curtain airbag 88A, flying of the rear-side garnish 86, and thus, the A-pillar garnish 64 inside the vehicle cabin 14 can be suppressed.

Furthermore, as illustrated in FIG. 1, the extension portion 69 is provided at the upper end portion of the front-side garnish 66, the extension portion 69 is provided so as to extend substantially toward the rear side of the vehicle and the rear end portion 69A is covered by the upper end portion of the rear-side garnish 86 (see also FIG. 3). In other words, the vehicle upper side of the space between the front-side garnish 66 and the rear-side garnish 86 has an outer appearance that is continuous with the front-side garnish 66 and the rear end portion 69A of the extension portion 69 is covered by the rear-side garnish 86, enabling a terminal end of the rear end portion 69A to be unnoticeable to occupants and provision of a neat appearance.

Also, as illustrated in FIG. 3, the tether clip 71 is provided at a position in the rear-side garnish 86, the position corresponding to the extension portion 69 of the front-side garnish 66, floating-up of the rear-side garnish 86 at the part in which the extension portion 69 of the front-side garnish 66 and the rear-side garnish 86 are laid on each other can be suppressed. Consequently, a quality in outer appearance of the A-pillar garnish 64 can be enhanced.

Furthermore, as illustrated in FIG. 4, each of the front-side garnish 66 and the rear-side garnish 86 has a substantially U-shape in a section orthogonal to the longitudinal direction of the A-pillar 24. Then, the wire harnesses 78 and the hose 80 are held between the front-side garnish 66 and the first pillar 26, and a part of the curtain airbag 88A is stored between the rear-side garnish 86 and the second pillar 28. In other words, the wire harnesses 78 and the hose 80 can efficiently be stored in the limited space between the A-pillar 24 and the A-pillar garnish 64 without hindering inflation and deployment of the curtain airbag 88A. Consequently, storage space efficiency can be enhanced.

Still furthermore, the flat wall 54, the thickness direction of which is substantially the vehicle width direction, is provided at a part on the vehicle cabin side of the second pillar 28, the part facing the curtain airbag 88A. In other words, the flat wall 54 is provided in the vicinity of the curtain airbag 88A. Therefore, when the curtain airbag 88A inflates and deploys, the curtain airbag 88A promptly receives a reaction force of the deployment from the flat wall 54, enabling the curtain airbag 88A to be quickly deployed toward the inner side substantially in the width direction of the vehicle, that is, the inner side of the vehicle cabin. Consequently, the capability of deployment of the curtain airbag 88A can further be enhanced.

Also, in the second pillar inner panel 40 that forms a part of the second pillar 28 and is formed so as to have a substantially L-shape in a section orthogonal to the longitudinal direction by the flat wall 54 and the vehicle front side surface 40C provided so as to extend from the flat wall 54 toward the outer side substantially in the width direction of the vehicle, an end surface of the end portion 40A in the direction orthogonal to the longitudinal direction is in abutment with the flat surface 52 of the end portion 44A in the direction orthogonal to the longitudinal direction of the second pillar outer panel 44 forming the other part of the second pillar 28. Therefore, the need for a flange for joining the second pillar outer panel 44 and the second pillar inner panel 40, the flange projecting to the outside of the A-pillar 24, is eliminated at least for one of end portions in the direction orthogonal to the longitudinal direction of the second pillar 28 of the A-pillar 24. Consequently, wider view during driving of the vehicle can be ensured.

Furthermore, as a result of the end surface of the end portion 40A in the direction orthogonal to the longitudinal direction of the second pillar inner panel 40 being in abutment with the flat surface 52 of the end portion 44A in the direction orthogonal to the longitudinal direction of the second pillar outer panel 44 forming the other part of the second pillar 28, the need for a flange projecting toward the outside of the A-pillar 24 is eliminated. Consequently, the sectional area of the A-pillar 24 formed by the second pillar inner panel 40 and the second pillar outer panel 44 can be increased. Therefore, support stiffness of the curtain airbag device 88 can be enhanced.

Still furthermore, the flat wall 54, which is a part of the second pillar 28, the part facing the curtain airbag 88A, has a substantially flat surface, and thus, storage space efficiency of the accommodation space S for the curtain airbag 88A, the accommodation space S being formed by the second pillar 28 and the A-pillar garnish 64 can be enhanced. Consequently, mountability of the curtain airbag 88A can be enhanced.

Although in the above-described embodiment, the wire harnesses 78 and the hose 80 are held between the front-side garnish 66 and the first pillar 26, only either of the wire harnesses 78 and the hose 80 may be held between the front-side garnish 66 and the first pillar 26.

Although the second pillar inner panel 40 has a configuration in which the end surface of the end portion 40A in the direction orthogonal to the longitudinal direction is in abutment with the flat surface 52 of the second pillar outer panel 44 forming the other part of the second pillar 28, the present disclosure is not limited to this case, and may have a configuration in which the end portion 40B is in abutment with a surface of the second pillar outer panel 44 or a configuration in which each of the end portions 40A, 40B is in abutment with a surface of the second pillar outer panel 44.

Although an embodiment of the present disclosure has been described above, it should be understood that: the present disclosure is not limited to the above embodiment; and various alterations other than the above are possible without departing the spirit of the present disclosure.

What is claimed is:

1. A curtain airbag device mounting structure comprising:
   a first pillar that is a part of a front pillar and extends substantially along a vehicle height direction;
   a second pillar that is another part of the front pillar, the second pillar being disposed on a rear side of a vehicle relative to the first pillar at a predetermined distance from the first pillar and extending substantially along the vehicle height direction;
   a transparent member that is bridged between the first pillar and the second pillar and enables an outside of the vehicle to be viewed from a driver seat;
   a curtain airbag device including a curtain airbag stored along a roof side rail and the second pillar, the curtain airbag being configured to be supplied with gas to inflate and deploy in a curtain-like fashion over a side portion of a cabin of the vehicle in case of a collision of the vehicle; and
   a front pillar garnish attached to a vehicle interior side of the front pillar, the front pillar garnish including a front-side garnish and a rear-side garnish, the front-side garnish being attached to the first pillar, the rear-side garnish being attached to the second pillar, the rear-side garnish being configured to cover the curtain airbag from a vehicle interior side of the curtain airbag and to hold the curtain airbag in a state in which the curtain airbag is apart from the second pillar.

2. The curtain airbag device mounting structure according to claim 1, wherein the rear-side garnish is attached to the second pillar via a tether clip.

3. The curtain airbag device mounting structure according to claim 2, wherein:
   the front-side garnish includes an extension portion at an upper end portion of the front-side garnish in the vehicle height direction, the extension portion extending toward the rear side of the vehicle, and including a rear end portion covered by an upper end portion of the rear-side garnish in the vehicle height direction; and
   the tether clip is attached to the extension portion at a position corresponding to the extension portion in the rear-side garnish.

4. The curtain airbag device mounting structure according to claim 1, wherein
   each of the front-side garnish and the rear-side garnish has a U-shape in a section orthogonal to a longitudinal direction of the front pillar and
   at least one of a wire harness and a hose is held between the front-side garnish and the first pillar, and a part of the curtain airbag device is stored between the rear-side garnish and the second pillar.

5. The curtain airbag device mounting structure according to claim 1, wherein
   the second pillar includes a reaction force surface at a part on a vehicle interior side of the second pillar, the part of the second pillar facing the curtain airbag, a thickness direction of the reaction force surface being substantially along a vehicle width direction.

6. The curtain airbag device mounting structure according to claim 5, wherein
   the second pillar includes:
      a pillar inner panel that is a part of the second pillar and has a L-shape in a section orthogonal to a longitudinal direction, the L-shape being formed by the reaction force surface and a extending surface, the extending surface extending outward in the vehicle width direction from the reaction force surface; and
      a pillar outer panel that is another part of the second pillar, an end surface of at least one of end portions of the pillar inner panel in a direction orthogonal to a longitudinal direction of the pillar inner panel being in contact with a surface of an end portion of the pillar outer panel in a direction orthogonal to a longitudinal direction of the pillar outer panel.

7. The curtain airbag device mounting structure according to claim 1, wherein a part of the second pillar includes a substantially flat surface, the part of the second pillar facing the curtain airbag.

8. A curtain airbag deployment method, the curtain airbag deployment method performable by a structure mounting a curtain airbag device including a rear-side garnish that is a part of a front pillar garnish and has a U-shape that opens to a front pillar side in a section orthogonal to a longitudinal direction, the U-shape being formed by a first side wall portion and a second side wall portion facing the first side wall portion, a curtain airbag stored in a folded state between the rear-side garnish and a pillar inner panel, and an inflator that activates to supply a gas to the curtain airbag upon detection or prediction of a collision of a relevant vehicle, the curtain airbag deployment method comprising:

(a) holding the rear-side garnish in a state in which the rear-side garnish is apart from the front pillar via initial inflation of the curtain airbag caused by the activation of the inflator;

(b) after the initial inflation, causing the curtain airbag to inflate and deploy from a gap between the rear-side garnish and the front pillar while pressing the first side wall portion and the second side wall portion of the rear-side garnish apart from each other; and (c) after the step of (b), inflating and deploying the curtain airbag toward an inner side of an interior of the vehicle from between the first side wall portion and the second side wall portion pressed apart from each other to inflate and deploy the curtain airbag in a curtain-like fashion over a side portion of the interior of the vehicle while withdrawing the rear-side garnish.

* * * * *